(12) United States Patent
Rathjen

(10) Patent No.: US 8,784,406 B2
(45) Date of Patent: Jul. 22, 2014

(54) OPHTHALMOLOGICAL PATIENT INTERFACE DEVICE

(75) Inventor: Christian Rathjen, Bremen (DE)

(73) Assignee: Ziemer Ophthalmic Systems AG (CH)

( * ) Notice: Subject to any disclaimer, the term of this patent is extended or adjusted under 35 U.S.C. 154(b) by 0 days.

(21) Appl. No.: 13/553,260

(22) Filed: Jul. 19, 2012

(65) Prior Publication Data

US 2013/0226158 A1 Aug. 29, 2013

Related U.S. Application Data

(60) Provisional application No. 61/604,149, filed on Feb. 28, 2012.

(51) Int. Cl.
*A61B 18/18* (2006.01)

(52) U.S. Cl.
USPC ............................................. 606/4

(58) Field of Classification Search
CPC ................. A61F 9/0089; A61F 9/013; A61F 2009/00872
USPC ............. 606/4, 5, 6, 10, 11, 12, 166; 604/294
See application file for complete search history.

(56) References Cited

U.S. PATENT DOCUMENTS

| | | | | |
|---|---|---|---|---|
| 5,112,328 | A | * | 5/1992 | Taboada et al. ..................... 606/4 |
| 5,490,849 | A | * | 2/1996 | Smith ................................. 606/5 |
| 6,059,772 | A | * | 5/2000 | Hsia et al. .......................... 606/4 |
| 6,090,100 | A | | 7/2000 | Hohla |
| 6,331,181 | B1 | | 12/2001 | Tierney et al. ................ 606/130 |
| 7,125,119 | B2 | | 10/2006 | Farberov |
| 2005/0288745 | A1 | | 12/2005 | Andersen et al. |
| 2006/0129140 | A1 | | 6/2006 | Todd et al. ........................ 606/1 |
| 2007/0179478 | A1 | * | 8/2007 | Dobschal et al. ................. 606/4 |

(Continued)

FOREIGN PATENT DOCUMENTS

| | | |
|---|---|---|
| DE | 10 2007 020 565 A1 | 10/2008 |
| DE | 10 2010 022 298 A1 | 12/2011 |

(Continued)

OTHER PUBLICATIONS

Partial European Search Report issued Feb. 11, 2014 for related European Patent Application No. 12 00 5283.

(Continued)

*Primary Examiner* — Gary Jackson
*Assistant Examiner* — Nathan J Jenness
(74) *Attorney, Agent, or Firm* — Ostrolenk Faber LLP

(57) ABSTRACT

An ophthalmological patient interface device (27), for application onto an eye (3) comprises a coupling part (21) for attaching mechanically the ophthalmological patient interface device (27) to an optical projection system (20) of an ophthalmological apparatus (1). The ophthalmological patient interface device (27) further comprises a firm, ring-shaped, and transparent contact part (272) configured to contact a ring-shaped peripheral surface area (B) of the cornea, when the ophthalmological patient interface device (27) is applied on the cornea, while leaving uncovered by the contact part (272) a round central surface area (C) of the cornea, surrounded by the peripheral surface area (B), and to let pass a laser beam (L1) from the optical projection system (20) through the contact part (272) into eye tissue (30) covered by the ring-shaped peripheral surface area (B) of the cornea, when the ophthalmological patient interface device (27) is coupled to the optical projection system (20).

10 Claims, 7 Drawing Sheets

(56) References Cited

U.S. PATENT DOCUMENTS

| | | | |
|---|---|---|---|
| 2009/0143842 A1 | 6/2009 | Cumbie et al. | |
| 2009/0187174 A1* | 7/2009 | Rathjen | 606/5 |
| 2010/0241107 A1 | 9/2010 | Vogler et al. | |
| 2010/0274228 A1* | 10/2010 | Mrochen et al. | 604/541 |
| 2012/0283557 A1 | 11/2012 | Berlin | |
| 2013/0103011 A1 | 4/2013 | Grant et al. | |

FOREIGN PATENT DOCUMENTS

| | | |
|---|---|---|
| EP | 0218427 A2 | 4/1987 |
| EP | DE 10349296 | 5/2005 |
| EP | DE 10349297 | 5/2005 |
| WO | WO 2005/048896 A1 | 6/2005 |
| WO | WO 2007/084602 | 7/2007 |
| WO | WO 2011/083358 A1 | 7/2011 |
| WO | WO 2013/053367 | 4/2013 |

OTHER PUBLICATIONS

Partial European Search Report issued Jan. 31, 2014 for related European Patent Application No. 12005288.1.

\* cited by examiner

OPHTHALMOLOGICAL PATIENT INTERFACE DEVICE

The present application claims benefit of and priority to U.S. Provisional Patent Application Ser. No. 61/604,149 filed Feb. 28, 2012 entitled Apparatus for Treating Eye Tissue with Laser Pulses, the entire content of which is hereby incorporated by reference herein.

BACKGROUND

1. Field of the Disclosure

The present invention relates to an ophthalmological patient interface device for application onto a cornea of an eye during treatment of the eye. Specifically, the present invention relates to an ophthalmological patient interface device comprising a coupling part configured to attach mechanically the ophthalmological patient interface device to an optical projection system of an ophthalmological apparatus.

2. Related Art

EP 1731120 describes an ophthalmological apparatus comprising a base station with a light source for generating laser pulses, and an application head which can be mounted on an eye having a light projector for the focused projection of the laser pulses for punctiform breakdown of eye tissue. The application head is attached to an articulated support which is connected moveably to the base station. The ophthalmological apparatus further comprises an optical transmission system for transmitting the laser pulses from the base station through the support arm to the light projector. EP 1731120 further discloses a transparent contact body with fastening means for fixing the contact body to the eye of a patient. The contact body can be mounted removably to the light projector of the ophthalmological apparatus, e.g. by means of a screw lock or a snap lock, and can be disposed or sterilized after use on a patient. The contact body makes it possible to place the cornea in a defined position with respect to the light projector so that a flap of the cornea may be cut equidistantly to the exterior surface of the cornea, for example. On the other hand, the mechanical deformation of the cornea caused by placing the contact body on the cornea may produce undesirable side effects such as corneal folds that disturb the focus behind the posterior surface of the cornea.

US 2010/0274228 describes a functional element that can be coupled to the eye by means of a suction ring. The functional element can be formed in the fashion of a container which can receive a liquid that is located during operation between the cornea of the eye and a lens. The functional element of US 2010/0274228 represents a liquid eye interface which does not cause mechanical deformations of the cornea that produce corneal folds. On the other hand, the liquid interface of US 2010/0274228 does not place the cornea in a sufficiently defined position with respect to a projection lens so that accurate corneal cuts can only be made by using complex imaging feedback systems and real-time position control during operation, while some corneal cuts cannot be performed with sufficient accuracy at all.

SUMMARY

It is an object of this invention to provide an ophthalmological patient interface device for application onto an eye during treatment of the eye, which ophthalmological patient interface device does not have at least some of the disadvantages of the prior art.

According to the present invention, these objects are achieved through the features of the independent claims. In addition, further advantageous embodiments follow from the dependent claims and the description.

An ophthalmological patient interface device for application onto a cornea of an eye during treatment of the eye comprises a coupling part configured to attach mechanically the ophthalmological patient interface device to an optical projection system of an ophthalmological apparatus.

According to the present invention, the above-mentioned objects are particularly achieved in that the ophthalmological patient interface device further comprises a firm, ring-shaped, and transparent contact part configured to contact a ring-shaped first surface area of the cornea, when the ophthalmological patient interface device is applied on the cornea for the treatment of the eye, while leaving uncovered by the contact part an inner second surface area of the cornea, surrounded by the first surface area of the cornea, and to let pass a laser beam from the optical projection system through the contact part into eye tissue covered by the ring-shaped first surface area of the cornea, when the ophthalmological patient interface device is coupled to the optical projection system for the treatment of the eye.

In an embodiment, the ring-shaped contact part comprises a reference surface configured to contact the cornea and place the ring-shaped first surface area of the cornea into a defined position with respect to the optical projection system, when the ophthalmological patient interface device is coupled to the optical projection system and applied on the cornea for the treatment of the eye. Thus, the position of the peripheral part of the cornea with respect to the optical projection system is defined by the ring-shaped contact part, making possible accurate cuts, without requiring an imaging system for guiding the focus of the laser beam, while the central part of the cornea is left uncovered and, therefore, mechanically undisturbed.

In a further embodiment, the ring-shaped contact part is configured to leave uncovered by the contact part the inner second surface area of the cornea, when the ophthalmological patient interface device is applied on the cornea for the treatment of the eye, such that a laser beam directed into eye tissue covered by the inner second surface area of the cornea, when the ophthalmological patient interface device is coupled to the optical projection system, travels from the optical projection system into the lens of the eye tissue, without passing through the contact part. Thus, the ophthalmological patient interface device has an open channel for letting pass the laser beam from the optical projection system into eye tissue covered by the central surface area of the cornea which is left uncovered by the ophthalmological patient interface device and, therefore, mechanically undisturbed. Consequently, in the central part of the cornea, there will be no occurrence of side effects, such as corneal folds, that disturb the focus behind the posterior surface of the cornea. Thus, in eye tissue below the central part of the cornea, focusing deep into the eye is possible, without disturbance of the focus, while precise cuts are possible in the peripheral area of the cornea.

In an embodiment, the ring-shaped contact part comprises a receiving surface which is averted from the reference surface and arranged such that, when the ophthalmological patient interface device is coupled to the optical projection system, a laser beam directed into eye tissue of the ring-shaped first surface area of the cornea travels from the optical projection system through the receiving surface and through the reference surface into the eye tissue, and a laser beam directed into eye tissue covered by the inner second surface area of the cornea travels from the optical projection system into the eye tissue without passing through the contact part.

In another embodiment, the ophthalmological patient interface device further comprises a wall extending from the contact part to the coupling part and encompassing a hollow space, the wall having an inlet for filling liquid into the hollow space when the ophthalmological patient interface device is applied on the cornea for the treatment of the eye.

In an embodiment, the wall is attached on the reference surface and at least part of the reference surface borders onto the hollow space such that, when the ophthalmological patient interface device is coupled to the optical projection system, a laser beam directed into eye tissue of the ring-shaped first surface area of the cornea travels from the optical projection system through the liquid filled into the hollow space, through the receiving surface and through the reference surface into the eye tissue, and a laser beam directed into eye tissue covered by the inner second surface area of the cornea travels from the optical projection system through the liquid filled into the hollow space into the eye tissue without passing through the contact part.

In another embodiment, the ophthalmological patient interface device further comprises a mirror arranged at an angle with respect to a projection axis of the optical projection system in an area between the coupling part and the contact part such that the laser beam projected by the optical projection system is deflected by the mirror when the ophthalmological patient interface device is attached mechanically to the optical projection system. The mirror of the ophthalmological patient interface device makes it possible to extend flexibly and easily the treatment area of an ophthalmological apparatus or add new treatment procedures, respectively, which would otherwise not be possible with conventional configurations.

In an embodiment, the ophthalmological patient interface device further comprises a device identifier which is detectable by a detector of the ophthalmological apparatus and enables control of the ophthalmological apparatus depending on the device identifier. For example, the device identifier comprises a mechanical device identifier, an optical device identifier, an electrical device identifier, and/or a contactless device identifier. For example, the device identifier is indicative of the type of the ophthalmological patient interface device, optical characteristics of the ophthalmological patient interface device, geometrical measures of the ophthalmological patient interface device, the refractive index of the ophthalmological patient interface device, the material of the ophthalmological patient interface device, the shape of the contact part, a mirror arranged in the ophthalmological patient interface device, the position of the mirror, and the angular arrangement of the mirror.

In a further embodiment, the ring-shaped contact part is configured to focus the laser beam from the optical projection system into the eye tissue, when the ophthalmological patient interface device is coupled to the optical projection system for the treatment of the eye.

In an embodiment, the ring-shaped contact part comprises two or more segments, two adjacent segments being separated by a gap.

BRIEF DESCRIPTION OF THE DRAWINGS

The present invention will be explained in more detail, by way of example, with reference to the drawings in which.

DETAILED DESCRIPTION OF THE EMBODIMENTS

Figure 1:
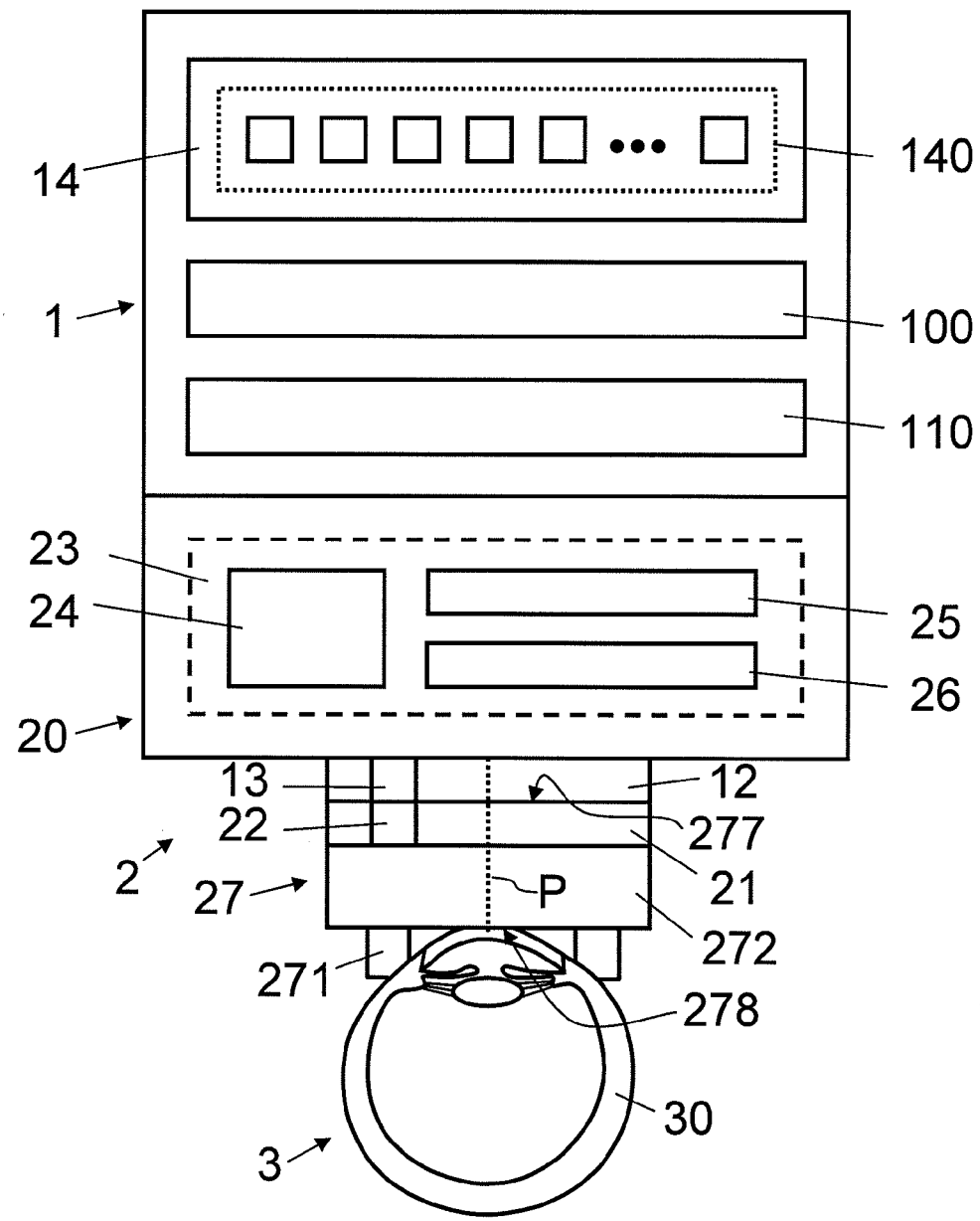
FIG. 1: shows a block diagram illustrating schematically an ophthalmological apparatus for treating eye tissue with laser pulses, the apparatus comprising an optical projection system with an ophthalmological patient interface device attached thereon.
Figure 2:
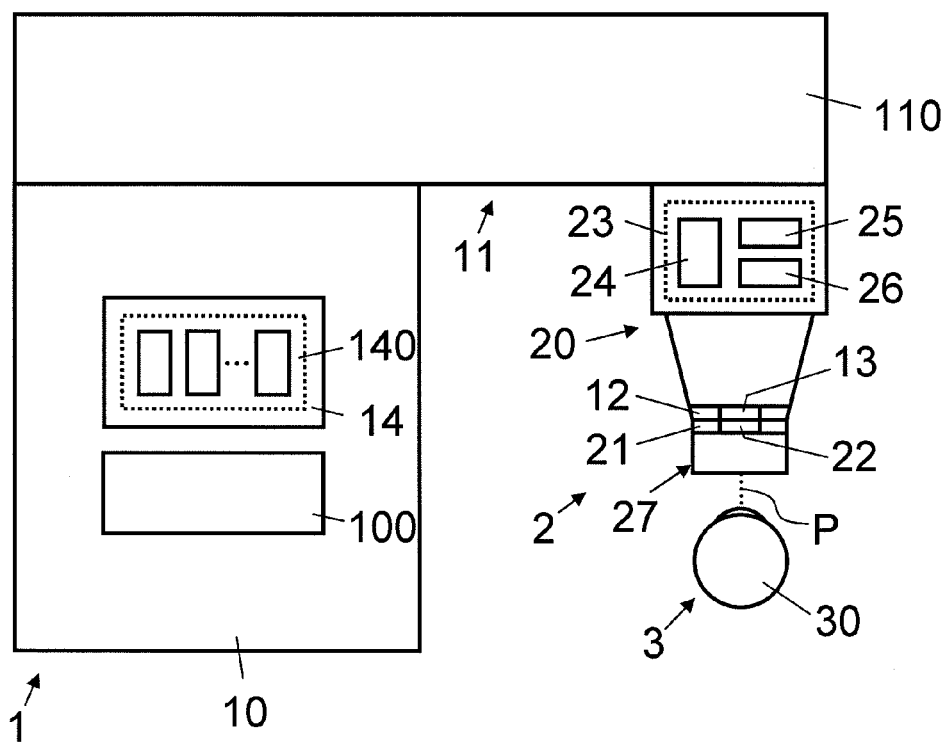
FIG. 2: shows a block diagram illustrating schematically the ophthalmological apparatus of FIG. 1 comprising a base station with a laser source and a support arm with the optical projection system and the ophthalmological patient interface device connected thereto.
Figure 3:
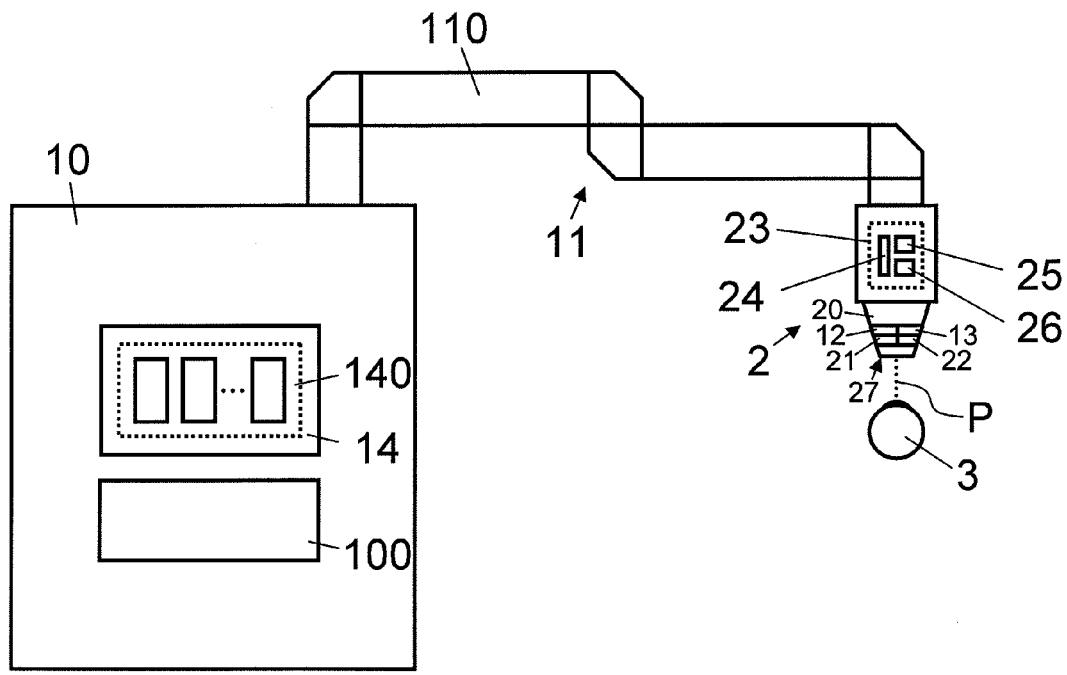
FIG. 3: shows a block diagram illustrating schematically the ophthalmological apparatus of FIG. 1 comprising a base station with a laser source and an articulated support arm for connecting the optical projection system and the ophthalmological patient interface device.
Figure 4:
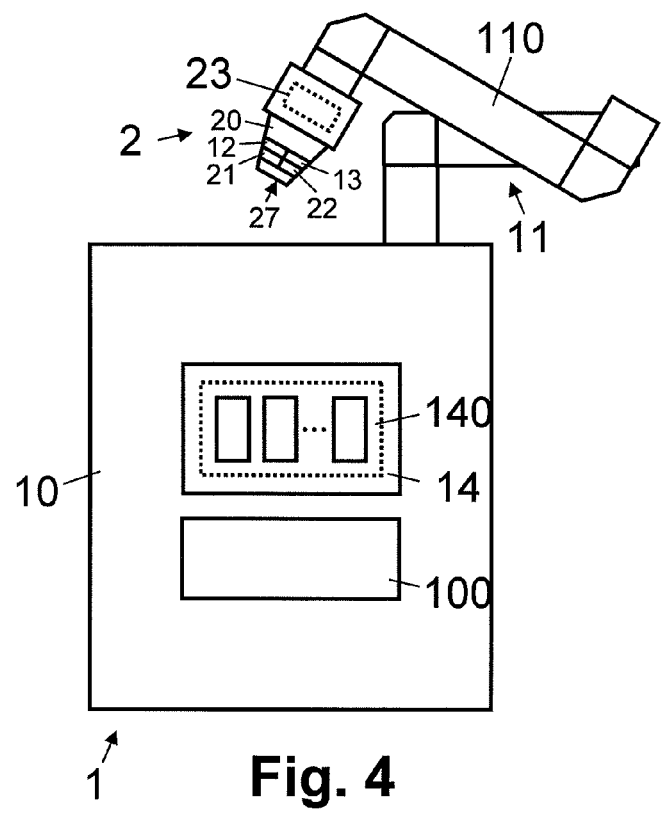
FIG. 4: shows a block diagram illustrating schematically the ophthalmological apparatus of FIG. 3 with a different positional adjustment of the articulated arm.

In FIGS. 1, 2, 3, 4, 5 and 8, reference numeral 1 refers to an ophthalmological apparatus for treating eye tissue 30 with laser pulses P. As is illustrated schematically in FIGS. 1, 2, 3, 4, 5 and 8, the ophthalmological apparatus 1 comprises a laser source 100 and a control module 14. Depending on the embodiment, the laser source 100 and the control module 14 are arranged in a base station 10, as shown in FIGS. 2, 3, 4, for example. The laser source 100 is configured to generate a pulsed laser beam L, L', L*, L1, L2, L3 (see FIG. 5, 8 or 9), e.g. a beam of femtosecond laser pulses P. In an embodiment, the laser source 100 is configured to generate a pulsed laser beam L, L', L*, L1, L2, L3 with a selectable wavelength in the IR-A-infrared range, the IR-B-infrared range, and/or the UVA-ultra violet range. Depending on the embodiment, the laser source 100 includes one or more lasers and/or a frequency modulation module for generating the laser beam L, L', L*, L1, L2, L3 with alternate wavelengths. For example, the control module 14 comprises a processor with data and program memory, the program memory having stored therein programmed software modules with computer program code for controlling the processor. One skilled in the art will understand that there are various alternatives for implementing the control module 14 by way of hardware and/or software modules.

As illustrated schematically in FIGS. 1, 2, 3, 4, 5 and 8, the ophthalmological apparatus 1 further comprises an optical transmission system 110 which is configured to transmit the laser pulses P from the laser source 100 to an optical application device 2. Depending on the embodiment, the optical transmission system 110 is arranged in a (flexible or inherently rigid) support arm 11 which is attached to the base station 10, as shown in FIGS. 2, 3, 4, for example, and the optical transmission system 110 is configured to transmit the laser pulses P from the laser source 100 to the optical application device 2 which is arranged at the end of the support arm 11 averted from the base station 10. For example, the support arm 11 is a flexible, articulated support arm, e.g. an articulated support arm as disclosed in EP 1 731 120 and illustrated in FIGS. 3 and 4, or an inherently rigid support arm, as illustrated in FIG. 2. The optical transmission system 110 comprises one or more scanning systems having one or more pivotable deflection mirrors for scanning a two dimensional (x, y) treatment area in the eye tissue 30 with the laser pulses P.

Preferably, the optical application device 2 comprises an optical projection system 20 and the optical transmission system 110 is configured to transmit the laser pulses P from the laser source 100 to the optical projection system 20. Different types of optical projection systems 20 have different optical characteristics such as focal distance, refraction power, field of view, and focusing systems 23 (described later in more detail), etc. The optical application device 2 is further provided with an ophthalmological patient interface device 27, which is a fixed, integral part of the optical application device 2 or, preferably, attached removeably to the optical application device 2, e.g. to the optical projection system 20.

For removeably attaching the ophthalmological patient interface device 27 to the ophthalmological apparatus 1, the optical projection system 20 comprises a coupling part 12 configured to attach mechanically the ophthalmological patient interface device 27 to the optical projection system 20. Correspondingly, the ophthalmological patient interface device 27 comprises a coupling part 21 configured to attach mechanically the ophthalmological patient interface device 27 to the optical projection system 20. By mechanically connecting the ophthalmological patient interface device 27 to the optical projection system 20, the ophthalmological patient interface device 27 is connected optically to the optical transmission system 110 and, thus, to the laser source 100. The coupling parts 12, 21 form a coupling system which makes it possible to connect different types of ophthalmological patient interface devices 27 removeably to the ophthalmological apparatus 1 and its optical transmission system 110. Depending on the embodiment, for the mechanical attachment/detachment, the coupling parts 12, 21 form a screw coupling system, a bayonet coupling system, a spring latch coupling system, a vacuum coupling system, or an electromagnetic force coupling system, for example.

As is further illustrated schematically in FIGS. 1, 2, 3, 4, 5, 6, 7 and 8, the ophthalmological patient interface device 27 comprises at least one device identifier 22 which is detectable by a detector 13 of the ophthalmological apparatus 1.

The device identifier 22 indicates and identifies a particular type of ophthalmological patient interface device 27. Herein, reference is made merely to one device identifier 22, one skilled in the art will understand, however, that depending on the embodiment there are multiple separate device identifiers 22 or one common device identifier 22 for identifying the type and various characteristics of the ophthalmological patient interface device 27. For example, the device identifier 22 is a mechanical or electrical device identifier 22, integrated in the coupling part 21 and detectable by a corresponding mechanical or electrical detector 13, integrated in the coupling part 12 of the optical projection system 20, respectively. Alternatively, the device identifier 22 is a contactless device identifier 22, e.g. an optical identifier or an RFID-identifier, and the detector 13 is a corresponding contactless detector, e.g. an optical or RFID detector. In the latter case, the device identifier 22 associated with the ophthalmological patient interface device 27 may be implemented as a unit separate from the ophthalmological patient interface device 27, e.g. as part of the packaging used to protect and sell the ophthalmological patient interface device 27.

The detector 13 is connected to the control module 14 via a signaling interface for transmitting to the control module 14 device identifier data, read or detected on or for the ophthalmological patient interface device 27 currently attached to the optical projection system 20. Accordingly, the device identifier 22 or respective device identifier data makes it possible for the control module 14 to determine the type of ophthalmological patient interface device 27 presently attached to the ophthalmological apparatus 1 or the optical projection system 20, respectively. In an embodiment, the coupling parts 12, 21 are further configured to establish a signaling interface between the ophthalmological apparatus 1 and the ophthalmological patient interface device 27 attached to the optical projection system 20.

The signaling interfaces between the control module 14 and the optical projection system 20 or the attached ophthalmological patient interface device 27, respectively, make it possible for the control module 14 to transmit control signals with control data and control commands to the optical application device 2, specifically to the optical projection system 20 and/or the ophthalmological patient interface device 27, as will be described later in more detail. Depending on the embodiment, the signaling interface is contact-based, including wires and electrical contact elements, or contact-less, including optical or RF connection modules.

As is shown in FIGS. 1, 2, 3, 4, 5 and 8, the optical application device 2 further comprises a focusing system 23 which is implemented as part of the optical projection system 20 or is arranged in the optical path upstream of the optical projection system 20. As is illustrated schematically in FIGS. 1, 2, 3, 4, 5 and 8, the focusing system 23 comprises two optical systems 25, 26, each comprising an arrangement of one or more optical elements, e.g. one or more lenses and/or mirrors. The optical systems 25, 26 are coupled with a driver system 24, comprising one or more electric motors. The driver system 24 is configured to adjust the optical systems 25, 26 individually, either sequentially or in parallel, such that the laser pulses P are projected onto a defined projection surface F, e.g. a projection plane, and focused on this projection surface F with a spot S having a defined spot size d, as will be described in the following paragraphs with reference to FIG. 9.

Figure 9:
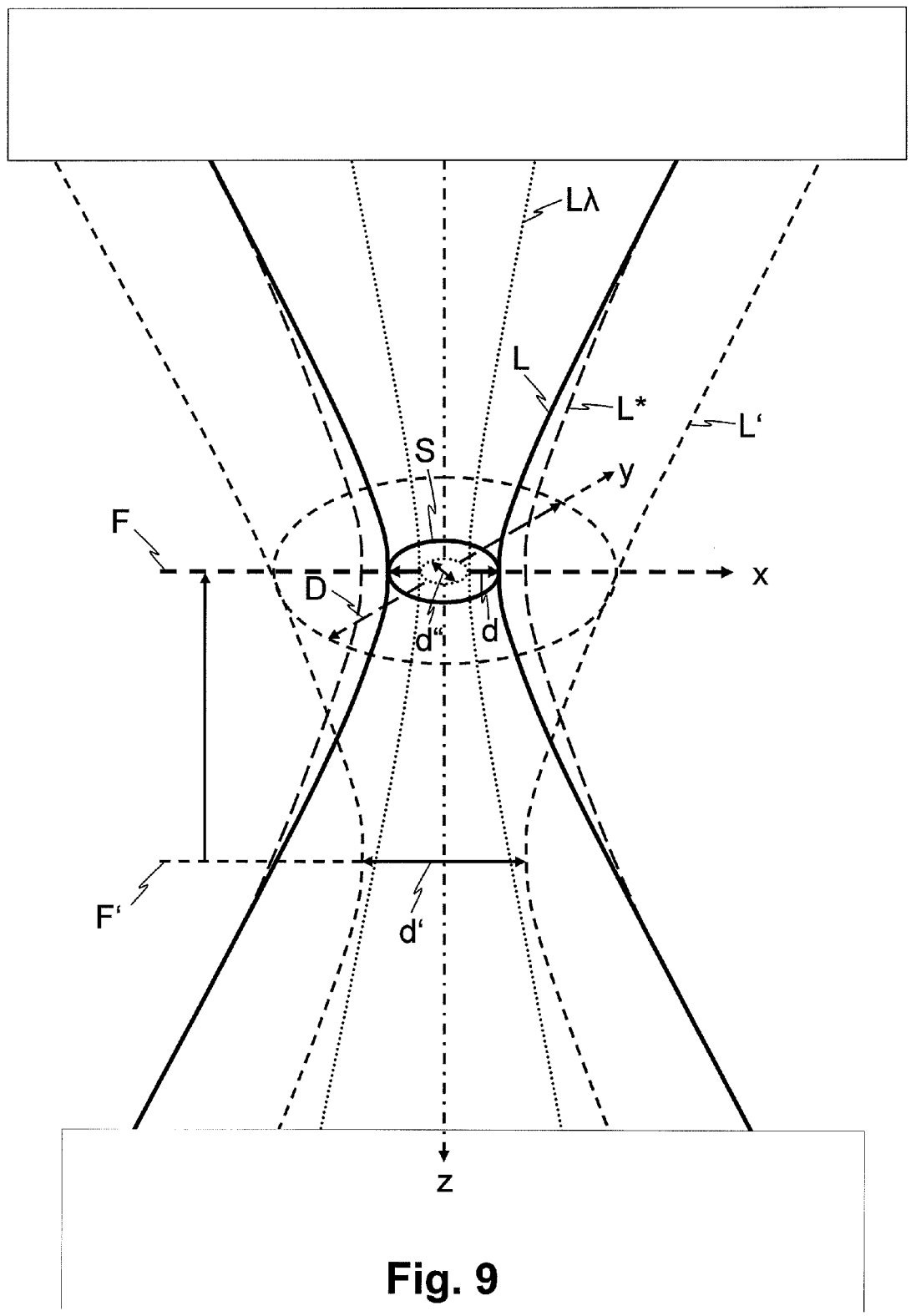
FIG. 9: shows a schematic diagram of profiles of a pulsed laser beam in different states where the pulsed laser beam is projected on different projection surfaces and focused on one of the projection surfaces with a defined spot size.

In FIG. 9, reference numerals L', L*, L refer to pulsed laser beams shown with their respective beam profiles, e.g. Gaussian beam profiles, at different states of the focusing system 23. Reference numeral L' refers to the pulsed laser beam in a first state where the narrowest section of the beam profile is projected onto projection surface F' with a spot size having a diameter d'. Thus, in the first state the pulsed laser beam L' is projected onto projection or imaging surface F'. In this first state, the beam profile on the upper projection surface F has a diameter D which is significantly larger than its diameter d' on the projection surface F'. Reference numeral L* refers to the pulsed laser beam in a second state where the narrowest section of the beam profile is projected on projection surface F with a spot size having a diameter d'. Accordingly in this second state, the pulsed laser beam L* is projected onto projection or imaging surface F. Alternatively, if the focusing system 23 remains unchanged, the first state of the pulsed laser beam L' corresponds to the ophthalmological apparatus 1 having attached a first type of optical application device 2 and/or ophthalmological patient interface device 27; whereas the second state of the pulsed laser beam L* corresponds to the ophthalmological apparatus 1 having attached a different second type of optical application device 2 and/or ophthalmological patient interface device 27. Reference numeral L refers to the pulsed laser beam in a third state where the narrowest section of the beam profile is projected on projection surface F with a spot size having a diameter d, which is significantly smaller than the diameter d' in the first and second states. Thus, in this third state, the pulsed laser beam L is projected and focused onto projection or imaging surface F with a spot size having a diameter d. In addition, reference numeral Lλ refers to the pulsed laser beam in the third state when the pulsed laser beam is generated with a different wavelength, generating on the imaging surface F a spot with an even smaller spot size having a diameter d"<d. One skilled in the art will understand that, generally, the imaging surface F is located in a different position when an alternate wavelength is used.

The control module 14 comprises different zooming functions 140 which are configured in each case to control the focusing system 23 to project the pulsed laser beam L or its laser pulses P, respectively, onto a projection surface F defined specifically for the respective zooming function 140 (defining a treatment depth), and to focus the pulsed laser beam L or its laser pulses P, respectively, onto this projection surface F with a spot size d (or d', d") defined specifically for the respective zooming function 140 (and a defined intensity profile in the cross section of the laser beam). As illustrated in FIG. 9, the projection surface F is associated with an x/y/z-coordinate system which can be defined with respect to the ophthalmological apparatus 1, e.g. the optical projection system 20, or the eye 3. The zooming functions 140 are configured to transmit to the focusing system 23 zooming control signals via the signaling interface. The zooming functions or zooming control signals, respectively, control the driver system 24 to adjust the optical systems 25, 26, either sequentially or in parallel, from an initial (first, second or other) state to the third state described above to project and focus the pulsed laser beam L or the laser pulses P, respectively, onto the defined projection surface F (at the defined treatment depth) with the defined spot size d (and intensity profile). Setting different zooming functions makes it possible to adapt flexibly and efficiently the operation of the ophthalmological apparatus to different types of ophthalmological patient interface devices used, for example, for different treatment procedures. Providing zooming functions 140 that control the focusing system 23 to project the pulsed laser beam L or its laser pulses P, respectively, onto a specific defined projection surface F with a specific defined spot size d (or d', d") makes it possible to adapt correctly the projection of the laser beam L or laser pulses P, respectively, to the typically non-linear transformation of the optical path through a first configuration, with a first ophthalmological patient interface device 27 applied on the eye tissue 30, to the optical path through a second configuration, with a different second ophthalmological patient interface device 27 applied on the eye tissue 30.

Specifically, the control module 14 is configured to receive or read from the detector 13 the device identifier 22 of the ophthalmological patient interface device 27 currently attached and connected to the optical projection system 20 or ophthalmological apparatus 1, respectively. The device identifier 22 or corresponding device identifier data, respectively, makes it possible for the control module 14 to determine the type of ophthalmological patient interface device 27. Depending on the device identifier 22 or type of ophthalmological patient interface device 27, the control module 14 selects and sets control parameters, selects and sets modes of operation, and/or selects and executes control functions, e.g. zooming functions 140. Thus, the control module 14 controls the ophthalmological apparatus 1 based on the device identifier 22.

Depending on the configuration and application, selecting different control parameters, modes of operation and/or control functions includes setting a different wavelength for the laser source 100 and, thus, generating laser pulses P with a different wavelength; setting a different projection or imaging surface F and, thus, a different treatment area effecting different parts of the eye with different eye tissue 30; and/or setting a different spot size d and, thus, a different type of treatment, e.g. precise tissue cuts or coarse tissue disruption and breakup. In an embodiment, different modes of operation are defined by a respective zooming function 140 and/or a respective wavelength of the laser beam L, L', L*, L1, L2, L3 generated by the laser source 100. For example, the control module is configured to use the device identifier 22 to select and set:

a first mode of operation for disrupting eye tissue 30 in the lens of the eye 3 using a first zooming function 140 to focus laser pulses P having a wavelength in the IR-A-infrared range, a second mode of operation for generating horizontal cuts in the cornea using a second zooming function 140 to focus laser pulses P having a wavelength in the UVA-ultraviolet range along a scan line, a third mode of operation for disrupting eye tissue 20 in the sclera or clouded cornea using a third zooming function 140 to focus laser pulses P having a wavelength in the IR-B-infrared range, a fourth mode of operation for generating cuts in the capsule using a fourth zooming function 140 to focus laser pulses P having a wavelength in the UVA-ultraviolet range along a scan line, a fifth mode of operation for generating vertical cuts in the cornea using a fifth zooming function 140 to focus laser pulses P having a wavelength in the IR-A-infrared range, and/or a sixth mode of operation for generating cuts in the lens of the eye 3 using a sixth zooming function 140 to focus laser pulses P having a wavelength in the IR-A-infrared range along a scan line.

In the following paragraphs, various different types of ophthalmological patient interface devices 27 with various different characteristics, as indicated and identified by the device identifier 22, are described with reference to FIGS. 1, 2, 3, 4, 5, 6, 7, and 8. Common to all these types of the ophthalmological patient interface devices 27 is the feature that in the applied state of the ophthalmological patient interface devices 27 for treating the eye 3, the ophthalmological patient interface device 27 is in contact with eye tissue 30. Thus, as illustrated explicitly in FIGS. 1, 5, 6, 7, and 8, the ophthalmological patient interface device 27 comprises a contact part 272 with a reference surface 278 which is configured and arranged to be in contact with the eye 3, e.g. with the cornea, or a protection foil placed on the eye 3, e.g. on the cornea, in the applied state of the ophthalmological patient interface device 27 during treatment of the eye 3.

Figure 5:
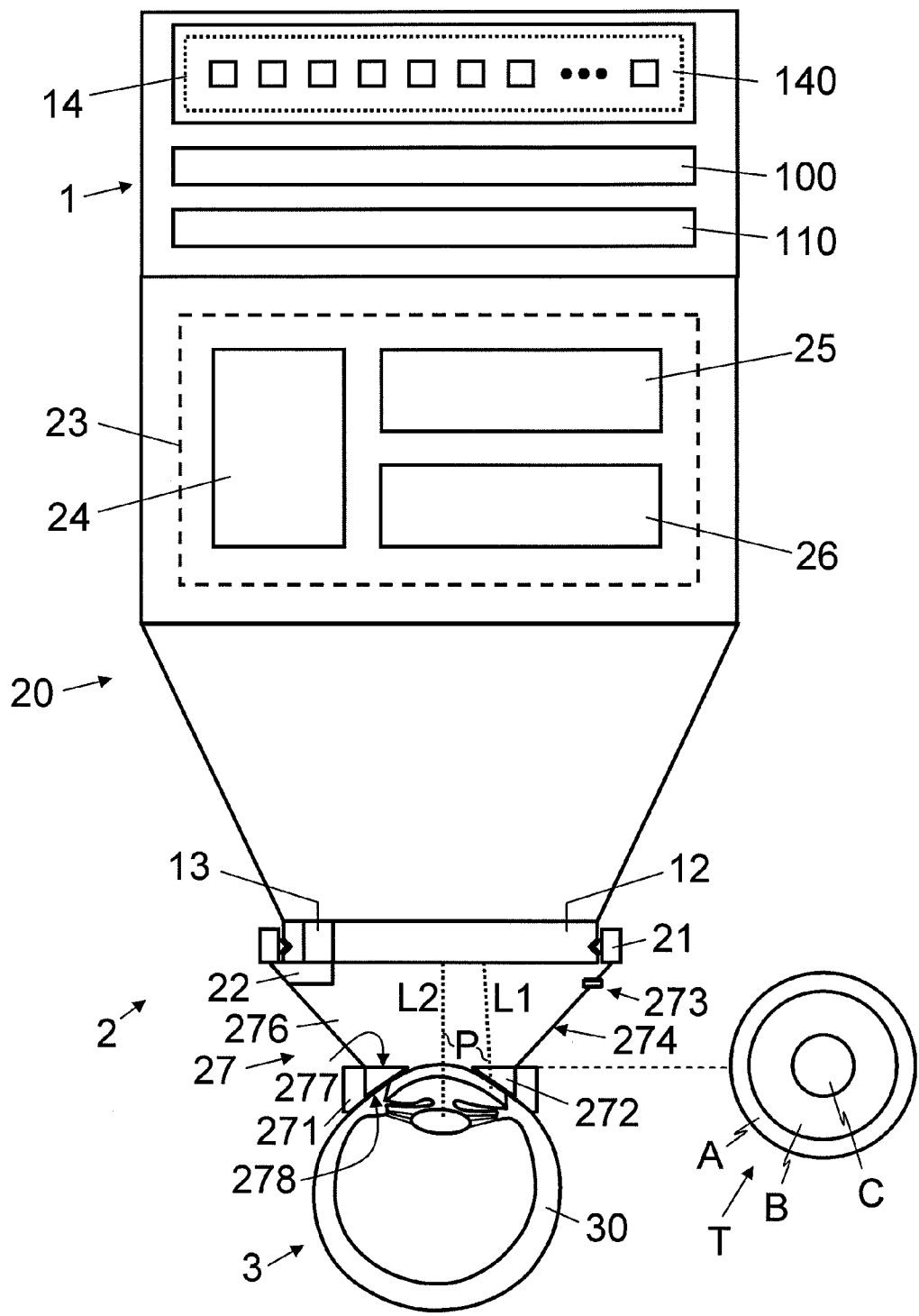
FIG. 5: shows a block diagram illustrating schematically the ophthalmological apparatus of FIG. 1 with an ophthalmological patient interface device having a ring-shaped contact part and a hollow space.
Figure 6:
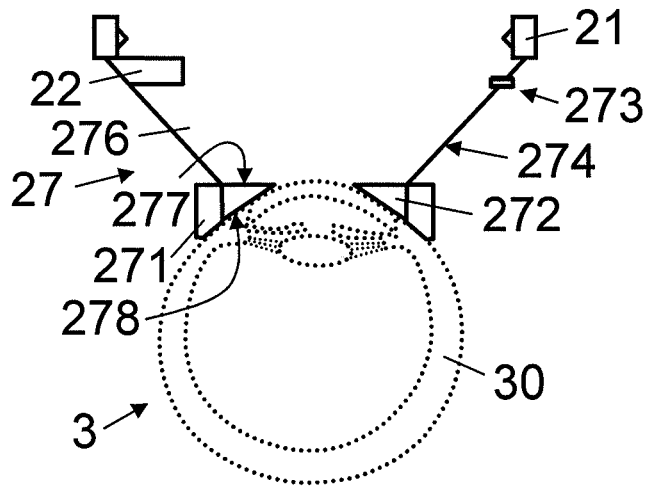
FIG. 6: shows a block diagram illustrating schematically the ophthalmological patient interface device with the ring-shaped contact part and hollow space.

Moreover, as illustrated schematically in FIGS. 1, 5, 6, 7, and 8, the ophthalmological patient interface device 27 preferably comprises fastening means 271, e.g. a fastening element such as a suction ring or suction ring segments, for fastening the ophthalmological patient interface device 27 to the eye 3, e.g. to a ring-shaped surface are A of the eye 3, as illustrated in top view T of the cornea in FIG. 5.

As illustrated schematically in FIGS. 1, 2, 3 and 4, one type of the ophthalmological patient interface device 27 comprises a contact body with a reference surface 278 configured to place at least part of the cornea into a defined position with respect to the optical projection system 20, when the ophthalmological patient interface device 27 is coupled to the optical projection system 20 and applied on the cornea for the treatment of the eye 3. Depending on the shape of the contact body, the cornea is applanated by the contact body or given another desired shape, for example concave or convex. Moreover, the ophthalmological patient interface device 27 or the contact body, respectively, has a receiving surface 277 which is averted from the reference surface 278 and faces the optical projection system 20 when the ophthalmological patient interface device 27 is coupled to the optical projection system 20.

For this type of ophthalmological patient interface device 27, the device identifier 22 indicates interface characteristics such as thickness (in the direction of the projection axis of the optical projection system 20 between the reference surface 278 and the receiving surface 277), material, refraction index, shape, e.g. plane or curved (spherically, convexly), etc. Further characteristics indicated by the device identifier 22 include the presence and arrangement of integral parts of the contact body, e.g. mirror elements or other optical elements as described later in more detail in the context of FIGS. 7 and 8.

As illustrated schematically in FIGS. 5, 6, 7 and 8, another type of the ophthalmological patient interface device 27 comprises a ring-shaped contact part 272 which is either a continuous non-interrupted ring or a ring composed of several ring segments which are separated by gaps between two adjacent ring segments. The ring-shaped contact part 272 has a reference surface 278 which is in contact with a ring-shaped, peripheral surface area of eye tissue 30, e.g. a ring shaped, peripheral surface area B of the cornea as shown in top view T of the cornea in FIG. 5, when the ophthalmological patient interface device 27 is applied for the treatment of the eye 3, while leaving uncovered by the contact part 272 an inner, round, central surface area of eye tissue 30, e.g. an inner, round, central surface area C of the cornea as shown in top view T of the cornea in FIG. 5, which is surrounded by the covered ring-shaped surface area B. The reference surface 278 is arranged and shaped to place the ring-shaped surface area B contacted by the contact part 272 into a defined position with respect to the optical projection system 20 when the ophthalmological patient interface device 27 is coupled to the optical projection system 20 and applied for the treatment of the eye 3. Averted from the reference surface 278, the contact part 272 comprises a receiving surface 277 which faces the optical projection system 20 when the ophthalmological patient interface device 27 is coupled to the optical projection system 20. The ring-shaped contact part 272 is made from a firm and transparent material and configured to let pass a laser beam L, L', L*, L1, L2, L3 from the optical projection system 20 through the contact part 272 into the eye tissue 30, e.g. into the cornea. Thus, as illustrated in FIG. 5, a laser beam L1 directed into eye tissue 30 covered by the ring-shaped surface area B will travel from the optical projection system 20 through the receiving surface 277 and subsequently through the reference surface 278 into the eye tissue 30. In an embodiment, the ring-shaped contact part 272 is configured to focus the laser beam L1 into the eye tissue 30. For example, for focusing the laser beam L1, the ring-shaped contact part 272 comprises diffractive optical elements. On the other hand, a laser beam L2 directed into eye tissue 30 covered by the round central surface area C will travel from the optical projection system 20 into the eye tissue 30, e.g. the lens, without passing through the contact part 272. The advantage of this configuration is that the central surface area C of the cornea or the central part of the cornea, respectively, is left uncovered by the ophthalmological patient interface device 27 and is thus mechanically undisturbed. Therefore, in the central part of the cornea, there will be no occurrence of side effects, such as corneal folds, that disturb the focus behind the posterior surface of the cornea. Thus, in eye tissue 30 below the central part of the cornea, focusing deep into the eye 3 is possible, without disturbance of the focus. On the other hand, the position of the peripheral surface area B of the cornea or the peripheral part of the cornea, respectively, is well defined by the ring-shaped contact part 272, making possible cuts of precise dimensions, without requiring an imaging system for precisely guiding the focus.

As further illustrated in FIGS. 5, 6, 7, and 8, the ophthalmological patient interface device 27 comprises a wall 274, e.g. of ring or cylindrical shape, which extends from the contact part 272 to the coupling part 21 and encompasses a hollow space 276. In a variant, the wall 274 has an inlet 273 for filling a liquid or gel into the hollow space 276 when the ophthalmological patient interface device 27 is applied for the treatment of the eye 3, and the wall 274 is also provided with one or more venting outlets.

As shown in FIGS. 5, 6, 7, and 8, the wall 274 is attached and arranged on the reference surface 278 such that at least part of the reference surface 278 is exposed to and borders onto the hollow space 276. Specifically, the reference surface 278 is arranged such that it is accessible directly by a laser beam L, L', L*, L1, L2, L3 when the ophthalmological patient interface device 27 is coupled to the optical projection system 20. Accordingly, as shown in FIG. 5, a laser beam L1 directed into eye tissue 30 covered by the ring-shaped surface area B will travel from the optical projection system 20 through the empty or liquid filled hollow space 276, through the receiving surface 277, and subsequently through the reference surface 278 into the eye tissue 30. On the other hand, a laser beam L2 directed into eye tissue 30 covered by the round central surface area C will travel from the optical projection system 20 through the empty or liquid filled hollow space 276 into the eye tissue 30, e.g. the lens, without passing through the contact part 272.

For the ophthalmological patient interface device 27 illustrated in FIGS. 5, 6, 7, and 8, the device identifier 22 indicates further interface characteristics such as dimensions, shape, location, material, and/or refraction index of the contact part 272; size, shape and/or location of the opening defined by the contact part 272; and/or shape and/or dimensions of the hollow space 276 defined by the wall 274.

Figure 7:
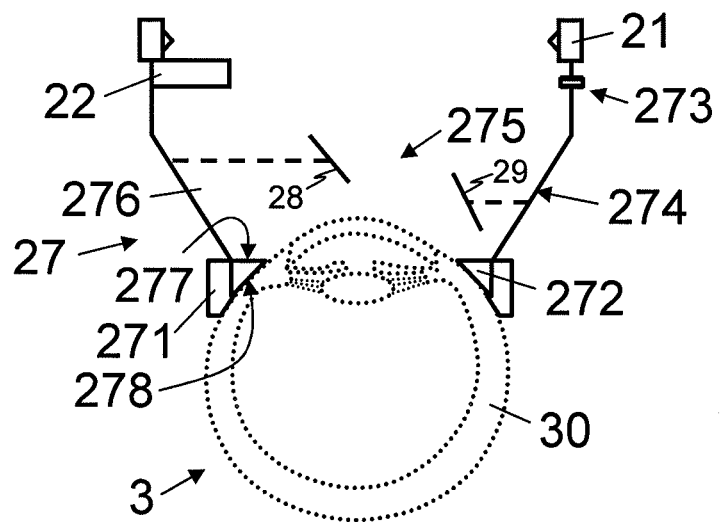
FIG. 7: shows a block diagram illustrating schematically the ophthalmological patient interface device with a mirror system arranged in the hollow space.
Figure 8:
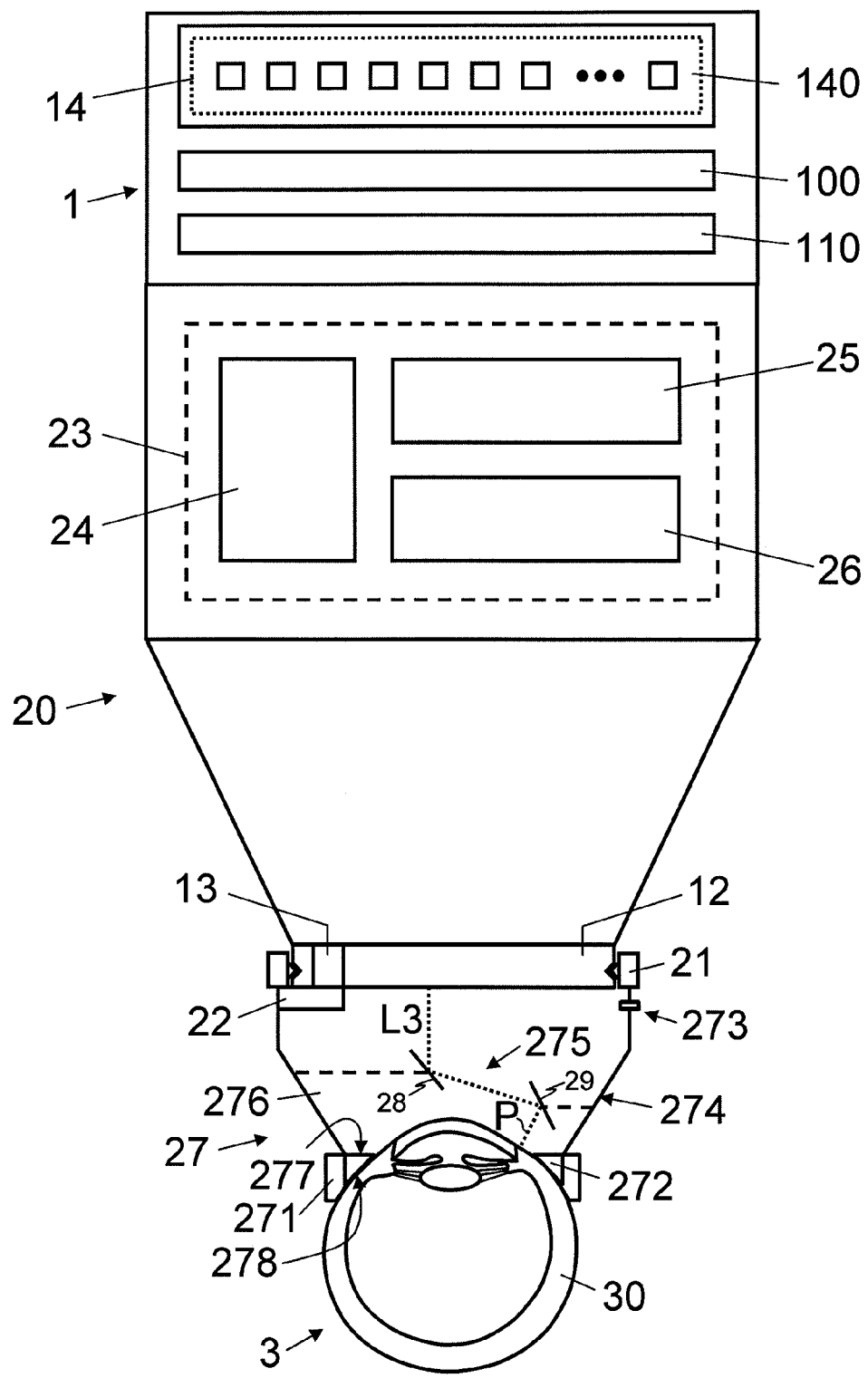
FIG. 8: shows a block diagram illustrating schematically the ophthalmological apparatus of FIG. 1 with an ophthalmological patient interface device having a ring-shaped contact part, a hollow space, and a mirror system arranged in the hollow space.

As illustrated in FIGS. 7 and 8, a further type of the ophthalmological patient interface device 27 comprises a mirror system 275 including at least one mirror 28, 29. The mirror system 275 is arranged downstream from the optical projection system 20 in the hollow space 276, when the ophthalmological patient interface device 27 is attached to the optical projection system 20. The mirror system 275 or its mirrors 28, 29, respectively, are attached to the ophthalmological patient interface device 27, for example by way of supporting elements connected to the wall 274 or the coupling part 21. In an alternative embodiment, the mirror system 274 or its mirrors 28, 29, respectively, are attached to the optical projection system 20, fixed or removeably, and inserted into the hollow space 276 when the ophthalmological patient interface device 27 is attached to the optical projection system 20. In a further embodiment, the mirror system is integrated in the contact body of the ophthalmological patient interface device 27 described above in the context of FIGS. 1, 2, 3, and 4. The mirror system 275 has at least one mirror 28, 29 or mirroring surface arranged at an angle with respect to a projection axis of the optical projection system 20 such that a laser beam L3 projected by the optical projection system 20 is deflected by the mirror system 275 away from the projection axis.

In the embodiment shown in FIGS. 7 and 8, the mirror system 275 comprises more than one mirror 28, 29 which are arranged in sequence such that the laser beam L3 projected by the optical projection system 20 is guided by the mirror system 275 to impinge the eye tissue 30 at a different angle than the projection axis and/or at a different location than the projection axis.

In an embodiment, the mirror system 275 comprises at least one mirror 28, 29 or mirroring surface which is rotatable about the projection axis of the optical projection system 20, e.g. manually or by way of a movement driver, such as an electric motor. In another embodiment, the mirror system 275 comprises at least one mirror 28, 29 with an adjustable deflection angle, e.g. manually or by way of a movement driver, such as an electric motor. In a further embodiment, the mirror system 275 comprises at least one mirror 28, 29 which is adjustable with a translatory movement to expand the working area in lateral direction. In case of motorized mirrors 28, 29, the control module 14 is further configured to control the rotational position, lateral position through translatory movement, and/or deflection angle, respectively, of the mirrors 28, 29 via the signaling interface.

Preferably, the sequentially arranged mirrors 28, 29 of the mirror system 275 are adjusted or adjustable to guide the laser beam L3 projected by the optical projection system 20 behind selected structures of the eye 3 without traversing the selected structures of the eye 3. For example, the mirror system 275 is configured or configurable to guide the laser beam L3 behind the Iris, the anterior chamber angle, the limbus, or the sclera, etc.

Arranging a mirror system 275 downstream from the optical projection system 20 makes it possible to extend flexibly and easily the treatment area of the ophthalmological apparatus 1 or add new treatment procedures, respectively, which would otherwise not be possible with conventional configurations.

For the of ophthalmological patient interface device 27 illustrated in FIGS. 7 and 8, the device identifier 22 indicates further interface characteristics such as the presence and configuration of the mirror system 275, including the number, location, size, and/or angular arrangement of its mirror(s) 28, 29 or other optical element(s).

In an embodiment, the wall 274 is attached to the ophthalmological apparatus 1 and extends from the optical projection system 20 to the coupling part 12. In this embodiment, the mirror system is attached to the ophthalmological apparatus 1 and arranged at least partly in the hollow space formed by the wall 274.

For the types of the ophthalmological patient interface device 27 that comprise a mirror system 275 which deflects the laser beam L3 from the optical projection system 20 away from the projection axis, the control module 14 comprises further zooming functions 140 which are configured to control the focusing system 23 depending on the current device identifier 22 or corresponding device identifier data, respectively, not only for a specific treatment depth (z-direction corresponding to the projection axis of the optical projection system 20) at the respective projection surface F, as described above with reference to FIG. 9, but also for a specific treatment location in the lateral x/y-direction, i.e. normal to the projection axis of the optical projection system 20.

The invention claimed is:

1. An ophthalmological patient interface device for application onto a cornea of an eye during treatment of the eye, the ophthalmological patient interface device comprising:
   a coupling part configured to attach mechanically the ophthalmological patient interface device to an optical projection system of an ophthalmological apparatus,
   a firm, ring-shaped, and transparent contact part configured to contact a ring-shaped first surface area of the cornea, when the ophthalmological patient interface device is applied on the cornea for the treatment of the eye, while leaving uncovered by the contact part an inner second surface area of the cornea, surrounded by the first surface area of the cornea, and to let pass a laser beam from the optical projection system through the contact part into eye tissue covered by the ring-shaped first surface area of the cornea, when the ophthalmological patient interface device is coupled to the optical projection system for the treatment of the eye, and
   a wall extending from the contact part to the coupling part and encompassing a hollow space for filling liquid into the hollow space when the ophthalmological patient interface device is applied on the cornea for the treatment of the eye,
   the contact part having a reference surface for contacting the cornea and a receiving surface which is averted from the reference surface,
   at least part of the receiving surface bordering onto the hollow space such that, when the ophthalmological patient interface device is coupled to the optical projection system, when said laser beam is directed into said eye tissue of the ring-shaped first surface area of the cornea, said laser beam travels from the optical projection system through the liquid filled into the hollow space, through the receiving surface and through the reference surface into the eye tissue, and when said laser beam is directed into eye tissue covered by the inner second surface area of the cornea, said laser beam travels from the optical projection system through the liquid filled into the hollow space into the eye tissue without passing through the contact part.

2. The ophthalmological patient interface device of claim 1, wherein the reference surface is further configured to contact the cornea and place the ring-shaped first surface area of the cornea into a defined position with respect to the optical projection system, when the ophthalmological patient interface device is coupled to the optical projection system and applied on the cornea for the treatment of the eye.

3. The ophthalmological patient interface device of claim 1, wherein the wall has an inlet for filling liquid into the hollow space when the ophthalmological patient interface device is applied on the cornea for the treatment of the eye.

4. The ophthalmological patient interface device of claim 3, wherein the wall is attached on the receiving surface.

5. The ophthalmological patient interface device of claim 1, further comprising a mirror arranged at an angle with respect to a projection axis of the optical projection system in an area between the coupling part and the contact part such that the laser beam projected by the optical projection system is deflected by the mirror when the ophthalmological patient interface device is attached mechanically to the optical projection system.

6. The ophthalmological patient interface device of claim 1, further comprising a device identifier which is detectable by a detector of the ophthalmological apparatus and enables control of the ophthalmological apparatus depending on the device identifier.

7. The ophthalmological patient interface device of claim 6, wherein the device identifier comprises at least one of: a mechanical device identifier, an optical device identifier, an electrical device identifier, and a contactless device identifier.

8. The ophthalmological patient interface device of claim 6, wherein the device identifier is indicative of at least one of: a type of the ophthalmological patient interface device, optical characteristics of the ophthalmological patient interface device, geometrical measures of the ophthalmological patient interface device, a refractive index of the ophthalmological patient interface device, a material of the ophthalmological patient interface device, a shape of the contact part, a mirror arranged in the ophthalmological patient interface device, a position of the mirror, and an angular arrangement of the mirror.

9. The ophthalmological patient interface device of claim 1, wherein the ring-shaped contact part is configured to focus the laser beam from the optical projection system into the eye tissue, when the ophthalmological patient interface device is coupled to the optical projection system for the treatment of the eye.

10. The ophthalmological patient interface device of claim 1, wherein the ring-shaped contact part comprises two or more segments, two adjacent segments being separated by a gap.

* * * * *